(12) United States Patent
Martinez et al.

(10) Patent No.: US 12,146,127 B1
(45) Date of Patent: Nov. 19, 2024

(54) METHOD FOR DRYING HIGH PROTEIN PRODUCTS FROM ETHANOL FERMENTATION

(71) Applicant: Shockwave Technologies Holding, LLC, Des Moines, IA (US)

(72) Inventors: Gustavo Martinez, Des Moines, IA (US); Joseph Fitzgerald, Des Moines, IA (US); John Lovato, Sausalito, CA (US)

(73) Assignee: SHOCKWAVE TECHNOLOGIES HOLDING, LLC, Des Moines, IA (US)

( * ) Notice: Subject to any disclaimer, the term of this patent is extended or adjusted under 35 U.S.C. 154(b) by 596 days.

(21) Appl. No.: 17/174,535

(22) Filed: Feb. 12, 2021

Related U.S. Application Data

(60) Provisional application No. 62/976,096, filed on Feb. 13, 2020.

(51) Int. Cl.
| | | |
|---|---|---|
| *C12P 13/00* | (2006.01) | |
| *C12F 3/10* | (2006.01) | |
| *C12M 1/00* | (2006.01) | |
| *C12P 1/00* | (2006.01) | |

(52) U.S. Cl.
CPC ............... *C12F 3/10* (2013.01); *C12M 47/14* (2013.01); *C12P 1/00* (2013.01)

(58) Field of Classification Search
CPC ....... C12P 2203/00; C12P 1/00; C12M 47/10; C12M 47/14; C12F 3/10
USPC .......................................................... 432/14
See application file for complete search history.

(56) References Cited

U.S. PATENT DOCUMENTS

| | | |
|---|---|---|
| 7,297,236 B1 | 11/2007 | Vander Griend |
| 8,986,551 B2 | 3/2015 | Kohl et al. |
| 9,180,463 B1 | 11/2015 | Fitzgerald |
| 9,375,731 B2 | 6/2016 | Dieker et al. |
| 10,093,891 B2 | 10/2018 | Kohl et al. |
| 10,266,790 B2 | 4/2019 | Lee |
| 10,392,590 B1 | 8/2019 | Jakel et al. |
| 2017/0107452 A1 | 4/2017 | Dasari et al. |

OTHER PUBLICATIONS

Assatory et al. Trend in food sci and tech. 2019, 86, pp. 340-351 . . .*

* cited by examiner

*Primary Examiner* — Robert B Mondesi
*Assistant Examiner* — Mohammad Y Meah
(74) *Attorney, Agent, or Firm* — Ryan T. Grace; Advent, LLP

(57) ABSTRACT

A method for drying high protein products of ethanol fermentation such as high protein thin stillage by combining wet high protein product with dry high protein product and passing the combined high protein product through a venturi.

13 Claims, 3 Drawing Sheets

METHOD FOR DRYING HIGH PROTEIN PRODUCTS FROM ETHANOL FERMENTATION

BACKGROUND

Ethanol may be produced by fermentation and distillation from biomass such as corn, for example. FIG. 1 illustrates the main steps of a method of processing corn into ethanol and products. The process 10 may begin by subjecting corn 20 to dry milling 30. A fermentation step 40 follows, which turns most of the corn starch into ethanol 60 and distillation 50 isolates the ethanol 60 from the nonfermented elements of the corn (whole stillage 70). Whole stillage 70 may be used as supplemental animal feed as is but because it has a moisture content of about 60-70% it is susceptible to the growth of undesirable organisms such as mold and mildew when exposed to air for a period of time. This also makes it expensive to ship.

In order to decrease the moisture content of whole stillage 70, it is commonly separated by centrifugation 80 into solids (termed distillers wet grains—DWG- or wet cake 100) and solubles (thin stillage 90). DWG 100 contains fiber and other insolubles. Thin stillage 90 contains proteins, soluble fiber, fats, and other solubles. The DWG can be dried to render it less susceptible to spoilage (DDG-distillers dried grains).

Since thin stillage 90 is a liquid it may be further processed by water evaporation 110, for example, to condense the thin stillage and produce a syrup 120 which may be sold separately as an animal feed. Syrup 120 may also be recombined with DWG 100 to produce distillers wet grains with solubles (DWGS) 140. DWGS may be dried (step 150) to produce distillers dried grains with solubles (DDGS) 160.

The ethanol industry is increasing production of high protein products using a variety of processes, generally by either treating corn pre-fermentation to remove nonfermentable starches or by treating thin stillage to separate protein and nonprotein elements. These higher relative protein byproducts have at least one characteristic in common, which is that they are difficult to dry using conventional dryers. While conventional DWGS may be dried using conventional methods such as a steam tube dryer, for example, high protein DWGS tends to ball up/clump up in a conventional steam tube dryer. The heat and residence time that is needed for adequate drying may also denature the proteins, resulting in a less desirable product. High protein thin stillage or syrup presents similar problems.

It would be beneficial to have a method for drying high protein ethanol fermentation products which avoids these issues.

SUMMARY

This summary is provided solely as an introduction to subject matter that is fully described in the detailed description and drawings. The summary should not be considered to describe essential features nor be used to determine the scope of the claims. Moreover, it is to be understood that both the summary and the detailed description are examples and explanatory only and are not necessarily restrictive of the subject matter claimed.

Several high protein products may be produced from the process of corn fermentation. The term "high protein product" as used herein means a material produced during a grain fermentation process which has a protein content higher than about 40% on a dry basis. It should be understood that the high protein product could be produced during processes other than fermentation and through fermentation of materials other than corn.

Ethanol producers presently have difficulties drying high protein thin stillage and high protein DWGS using existing dryers because the high protein content causes the material to clump, leading to ineffective drying. Moreover, the high heats and residence time required can denature the heat sensitive proteins. A solution presented here, in one aspect, is to use a venturi in combination with an airflow generator. In this configuration, the airflow generator is used to pull material through the venturi. In another aspect, a solution presented herein is to insert a pretreatment step to both reduce moisture and to reduce particle size or declump the material. The pretreatment involves blending the wet high protein product with an amount of dry high protein material, to yield a blended material that is more of a crumble as opposed to large clumps, prior to passage through the venturi. The combination of the blended material and/or venturi and airflow generator results in a material that can be further dried using a conventional existing dryer.

BRIEF DESCRIPTION OF THE DRAWINGS

The system briefly described above will be better understood by reference to the accompanying drawings. The drawings provide information concerning typical embodiments of the disclosure and are not therefore to be considered limiting of its scope.

DETAILED DESCRIPTION

Figure 1:
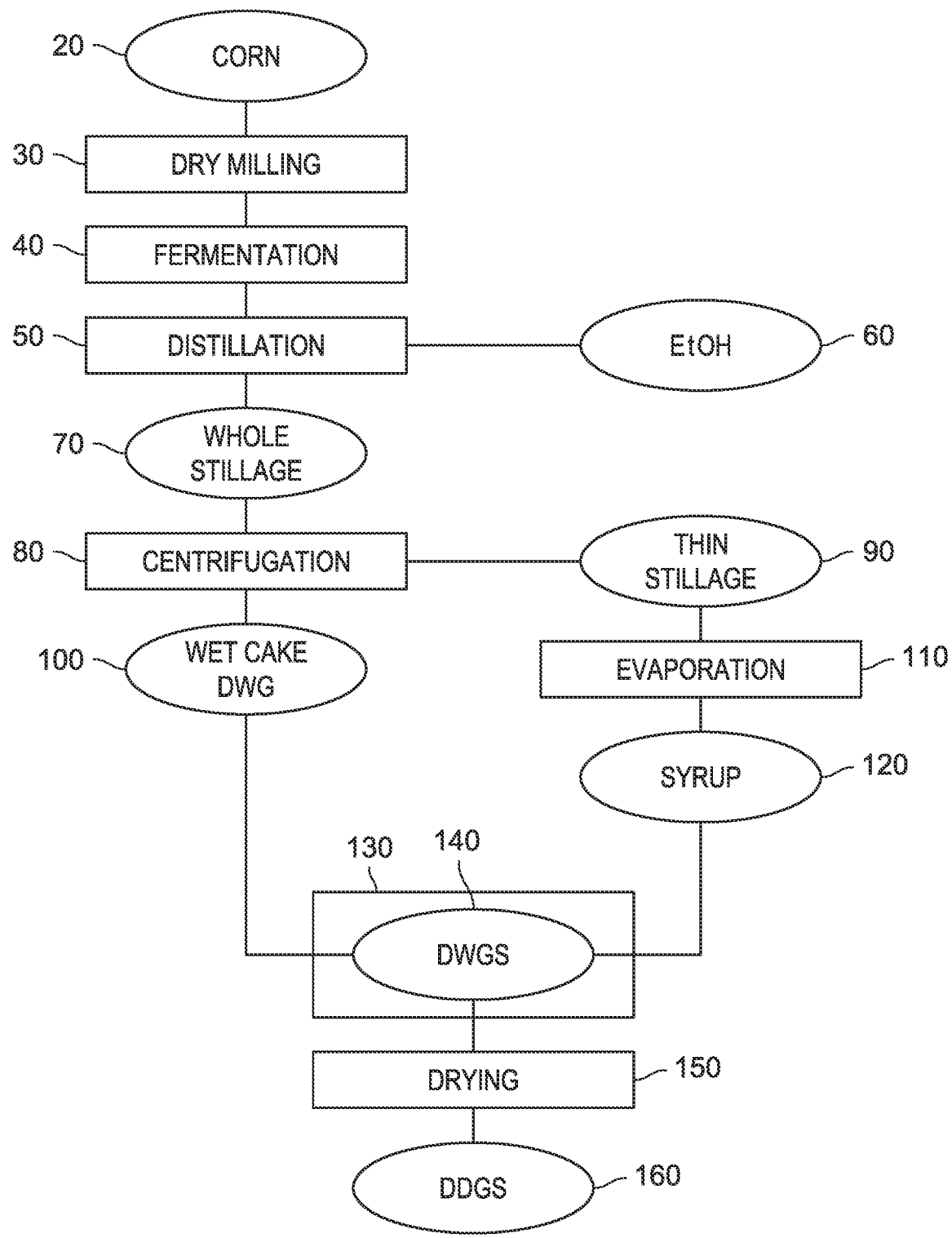
FIG. 1 is a schematic of a prior art corn fermentation process.

Reference is now made to the figures in which like reference numerals refer to like elements. Throughout the specification, reference to one embodiment or an embodiment means that a particular described feature, structure, or characteristic is included in at least one embodiment of the present disclosure Thus, appearances of the phrases in one embodiment or in an embodiment in various places throughout this specification are not necessarily all referring to the same embodiment. Furthermore, the described features, structures, or characteristics may be combined in any suitable manner in one or more embodiments. Those skilled in the art will recognize that the disclosure can be practiced without one or more of the specific details, or with other methods, components, materials, etc. In other instances, well-known structures, materials, or operations are not shown or not described in detail to avoid obscuring aspects of the disclosure.

Corn primarily comprises starch, germ, fiber, and protein. Only the starch can be converted to ethanol and during a fermentation most of the starch is converted into ethanol 60. The whole stillage residue 70 is thus mostly fiber, protein, and oils. Since protein is soluble, most of the protein ends up in thin stillage 90 upon separation of the whole stillage 70 into soluble thin stillage 90 and insoluble wet cake 100 components. Various methods may be employed to produce a product having a relative higher percentage of protein.

In a method discussed in U.S. Pat. No. 10,266,790 to Fluid Quip, Inc., for example, a high protein product is produced by treatment of the thin stillage to separate a protein portion from other water soluble solids. The protein portion is dewatered and dried to produce a protein product having at least 40% protein (all percentages are by weight unless otherwise noted) on a dry weight basis. The dewatered protein product has a protein content above 40% on a dry basis and a thick consistency similar to smooth peanut butter or molasses.

U.S. Pat. No. 8,986,551 to ICM, Inc. also teaches a method for processing thin stillage to create a high protein "fine suspended solids stream" that can be dewatered and sold as a product or added to wet cake and the combination dried to create high protein DDGS.

In another method of producing a high protein product, the corn may be subjected to a treatment prior to fermentation. This pretreatment may reduce the amount of unfermentable fiber in the corn. If this pretreated corn is processed through a conventional method as shown in FIG. 1, for example, the resulting products thin stillage, DWGS, and DDGS will be high protein (compared to non-pretreated corn). Generally, conventional DDGS contains about 30-35% protein on a dry basis. High protein DDGS contains above 40%.

General Method for Drying High Protein Products

Figure 2:
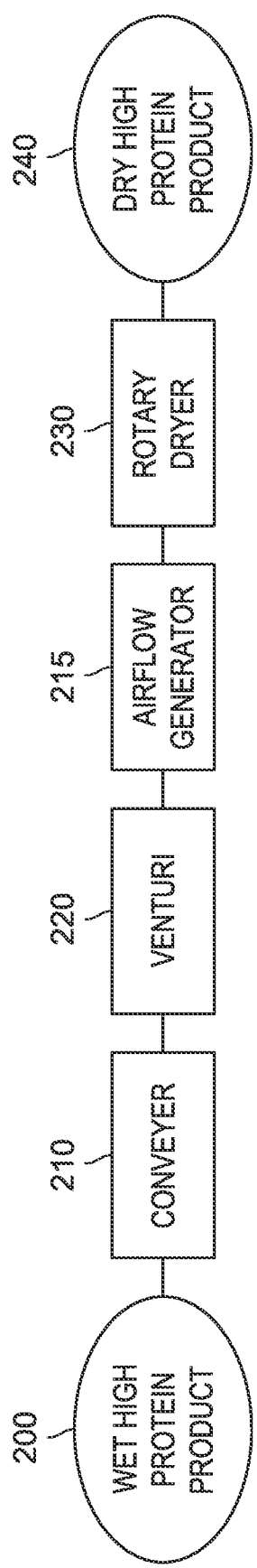
FIG. 2 is a schematic of a drying method described herein.

FIG. 2 illustrates a general inventive method for a drying high protein product which includes retrofitting an existing system. Wet high protein product 200 (perhaps made as described above) is carried on conveyer 210 to venturi 220. High protein product 200 is pulled through the venturi 220 using the airflow generator 215. In this system, airflow generator 215 is in line with the process flow so that the high protein product 200 passes through and may contact the airflow generator 215.

The combination of the venturi 220 and airflow generator 215 creates a low pressure environment which allows for water to evaporate at a lower temperature and in turn allows for drying at lower temperature (thus protecting proteins that are sensitive to heat).

Placement of the airflow generator 215 inline and after and close to the venturi 220 allows for maximum low pressure in the venturi. If the airflow generator 215 was further downstream or pushing rather than pulling airflow (in other words placed before the venturi rather than after) then the pressure in the venturi would be higher. Moreover, there are low pressure areas in the fan, to which the material is exposed, further increasing maximum exposure to a low pressure environment. Low pressure exposure means a lower temperature evaporation of product moisture which results in increased drying efficiency and less protein degradation.

This venturi treated high protein product may then be dried in a conventional dryer such as rotary dryer 230. Product is collected as dry high protein product 240.

The invention, in this embodiment, may be employed as a retrofitted system. In some cases a drying system may comprise a rotary dryer which does not adequately dry a high protein product, due to clumping of the wet high protein product. Insertion of the venturi 220 and airflow generator 215 into the process as described herein enables more effective drying of a wet high protein product.

In some aspects it may be desirable to pass the material through a second, or third, etc., venturi perhaps with a second or third, etc. airflow generator (not shown). In some cases, it can be desirable to produce a final product that has a moisture content less than that of the wet high protein product but not as low as produced using a venturi in combination with a rotary dryer.

Figure 3:
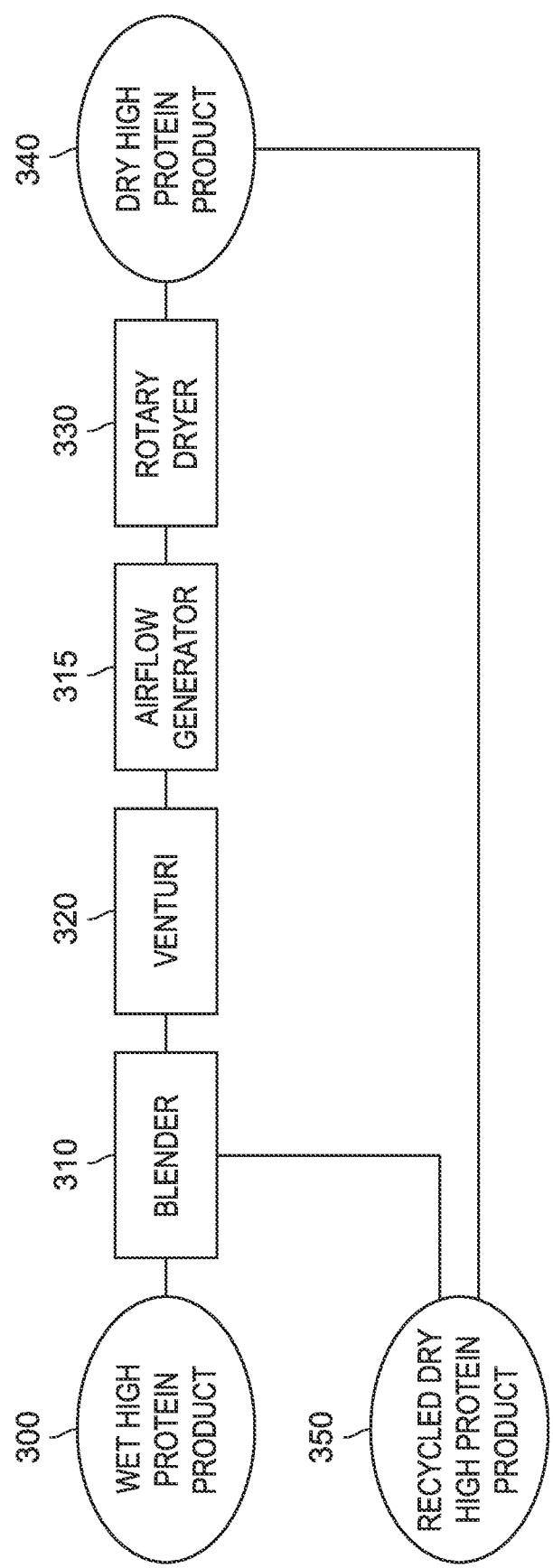
FIG. 3 is a schematic of a drying method described herein.

In another embodiment of the method, shown schematically in FIG. 3, some portion of dry high protein is combined with wet high protein product before passage through the venturi. For example, dry high protein product can be recycled through the process. In this process, recycled dry high protein product 350 is combined with wet high protein product 300 and blended in blender 310.

The blended combined high protein product 312 is then passed through venturi 320, using the airflow generator 315. As described above, airflow generator 315 is in line with the process flow so that the blended high protein product 312 passes through the airflow generator 315.

This venturi treated high protein product may then be dried in a conventional dryer such as rotary dryer 330. Product is collected as dry high protein product 340.

The combination of adding some dry high protein product to the wet starting material and the employment of the venturi in combination with the airflow generator minimizes clumping of the high protein product and facilitates drying. A lower temperature or shorter residence time may be then used in the rotary dryer.

This embodiment may also be employed as a retrofitted system.

Additional steps and equipment may be employed in the method for drying high protein products. For example, one or more dryers and air purifiers may be employed before and/or after the venturi and the rotary dryer. Cyclone dryers, dryer baghouses, conveyors may be employed.

Wet high protein product may be any of the high protein products described above such as a treated thin stillage product or a product produced after pretreatment of corn to reduce fiber. Wet high protein product may also be a DWGS product made by combining a high protein thin stillage product with DWG.

Wet high protein product may be from about 40 to 90% water, or from 40 to 80% water, or from about 60 to 80% water. The consistency may range from similar to smooth peanut butter to a cake like consistency, depending on the type of high protein product. For example, treated thin stillage has a consistency similar to peanut butter and high protein DWG has a consistency similar to cake.

Wet high protein product and recycled dry high protein product may be combined at a ratio from about 10 to 90% by weight dry to wet high protein product, desirably about 10 to 50%, desirably about 25 to 45% recycled dry product. Dry, recycled high protein product may have a water content less than about 40% and may be as low as 1 to 2%. The combined wet and dry high protein product may have a water content from about 30% to 70%, or from about 50 to 60%. All percentages herein are by weight unless otherwise noted.

The wet and dry high protein products may be combined in any type of mixer or blender that can effectively combine the components.

Venturi

Figure 4:
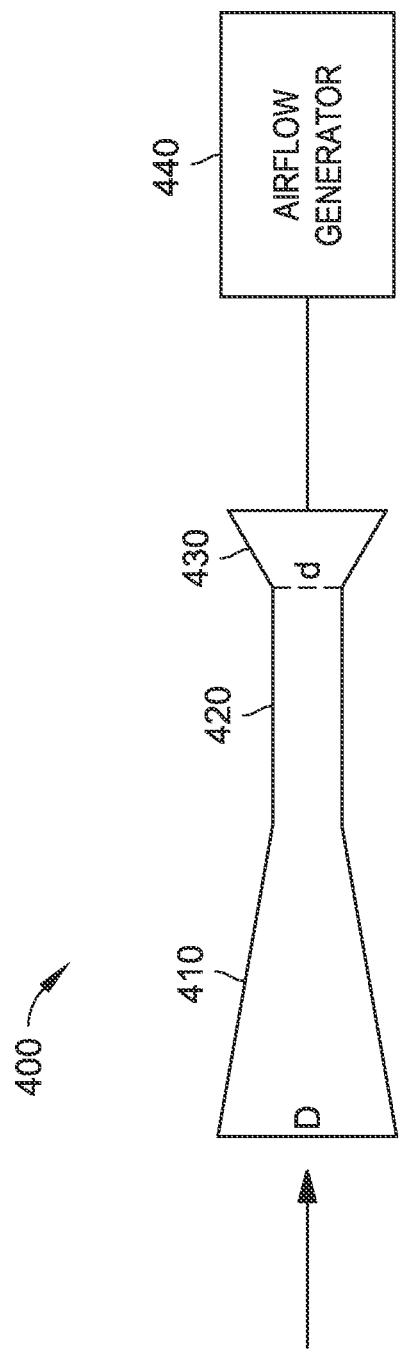
FIG. 4 is a schematic of a venturi and airflow generator as used in a method described herein.

As used herein, a venturi refers to a length of tubes or pipes which transitions from a first diameter to a second diameter, smaller than the first, then to a third diameter, which is larger than the second. The transitions may take place evenly over a longitudinal length of the venturi. Further, longitudinal sections of a venturi, for example the center section, may have substantially constant diameters. U.S. Pat. No. 9,180,463 describes a venturi, the principles of which can be used in the currently described method. FIG. 4 illustrates an example of a venturi 400. The ingress diameter D leading into the converging portion 410 may be about twice the egress diameter d. Converging portion 410 leads to a throat portion 420 which then diverges again into diverging portion 430 which may progressively increase in diameter along a length of the venturi in the direction of the airflow. In the present method, high protein product enters into the ingress portion 410 and exits at egress in portion 430. Other venturi configurations may be used, the relevant element is the constriction and deconstruction of the diameter. Passage of product through the venturi causes some drying and declumping of the material.

The venturi operation is generally as described in U.S. Pat. No. 9,180,463. An airflow generator (described further below) creates airflow along a path through the venturi. The velocity of the generated airflow may range from about 20 mph at the entry to the venturi to about 150 to 350 mph to 400 mph to supersonic within the venturi.

An air heater (not shown) can be used to heat the air in the system, generally at the point where the air and product enter the venturi. The air may be heated to a temperature from about 200 F to 1000 F, desirably about 400 F to 900 F, or about 400 F to 600 F. The temperature of the high protein product entering the venturi may be about 150 F to 200 F, desirably about 180 F to 190 F.

Certain embodiments have the throat diameter d of the venturi ranging from approximately 1.5" (38 mm) to approximately 6" (152 mm). The diameter D may thus range from about 3" to 12". The diameters are scalable based on material flow volume and may exceed these ranges.

Airflow Generator

The airflow generator may be embodied as a fan, an impeller, a turbine, a hybrid of a turbine and fan, a pneumatic suction system, a positive displacement blower or another suitable device for generating airflow, including devices configured to generate high speed airflow. In one aspect, the airflow generator is driven by a drive motor (not shown), can be disposed within a housing (not shown), and includes a plurality of radially extending blades (not shown) that rotate to generate a high speed airflow. The housing can couple with the venturi and can have a housing input aperture (not shown) that allows communication between the venturi and the interior of the housing. The blades define radially extending flow passages through which air passes to a housing outlet on its periphery to allow material to exit.

Dryer

The rotary dryer 230 may be a steam tube dryer, for example. The rotary dryer may be operated at a temperature of about 150 F to 200 F, or about 180 F to 190 F. Other types of dryers can be used, a rotary dryer is specifically mentioned because many producers currently use a rotary dryer and thus it may be easy to retrofit an existing system with the venturi and airflow generator. As an alternate embodiment, more than one venturi or other types of dryers could be used in sequence.

Example Implementations

Example 1-Process for Drying High Protein Product Made from Treatment of Thin Stillage High protein thin stillage can be obtained and processed through a method as shown in FIG. 2. On a dry basis, the protein content of the high protein thin stillage can be 60-68%, crude fat can be 4-6%, crude fiber can be 2-3%, and starch can be 1-3%. The materials can be combined at a ratio of about 0.35 dry to wet so that the blended material can have a moisture of 50-60% water.

| | 200 (wet high protein product) | 240 (dry high protein product) | Blended high protein product into venturi | Material post venturi & airflow generator |
|---|---|---|---|---|
| % water | 70% | 10% | 50-60% | 35-45% |

The airflow rate from the airflow generator pulling material into the venturi can be about 250 lbs/min. Temperature of the air into the venturi can be about 200 F, outlet temperature can be about 250 F; the temperature of the blended material upon entry into the venturi can be about 185 F and exiting temperature can be about 250 F.

After passage through the venturi, the partially dried material can be passed through a steam tube dryer at a temperature of about 185 F. Final product can have a moisture of about 10%. A portion of this product can be collected as dry high protein product and a portion recycled back through the method.

Example 2-Process for Drying DWGS Made Using High Protein Thin Stillage

High protein thin stillage made by one of the above methods can be reduced to a syrup and recombined with DWG. This high protein DWGS can then be processed as shown in FIG. 2 and generally as described in Example 1.

Example 3-Process for Drying High Protein Thin Stillage Made Using Corn Pretreatment As described above, nonfermentable fiber can be removed on the front end of the process, prior to corn fermentation. Since fiber is removed, the resulting whole stillage contains a higher percentage of protein. Accordingly, further processed thin stillage contains a higher percentage of protein. This higher protein thin stillage can be taken through the process shown in FIG. 2 and generally as described in Example 1.

Example 4-Process for Drying High Protein DWGS Using High Protein Thin Stillage Made Using Corn Pretreatment High protein thin stillage as described above using corn pretreatment to increase percentage protein can be reduced to a syrup and recombined with DWG. This high protein DWGS can then be processed as shown in FIG. 2 and generally as described in Example 1.

CONCLUSION

Modifications and variations will be apparent to those skilled in the art from the forgoing detailed description. All modifications and variations are intended to be encompassed by the following claims. All publications, patents, and patent applications cited herein are hereby incorporated by reference in their entirety.

Although the technology has been described with reference to particular embodiments, equivalents may be employed, and substitutions made herein without departing from the scope of the technology as recited in the claims. Components illustrated and described herein are merely examples that may be used to implement the embodiments of the disclosure and may be replaced with other embodiments without departing from the scope of the disclosure.

What is claimed is:

1. A method for drying high protein product from a fermentation process comprising:
   blending wet high protein product with dry high protein product to provide a blended high protein product; and
   passing the blended high protein product through at least one venturi, then through an airflow generator, and then a dryer, wherein the wet high protein product, the dry high protein product, and the blended high protein product include at least 40% protein by weight on a dry weight basis.

2. The method of claim 1, wherein the dry high protein product is a portion of the dry high protein product produced from the method and recycled.

3. The method of claim 1, wherein the airflow generator is after the venturi and acts to pull the blended high protein product through the venturi.

4. The method of claim 1, wherein the dryer is a rotary dryer.

5. The method of claim 1, wherein the airflow generator has an airflow velocity ranging from about 150 mph to supersonic.

6. The method of claim 1, wherein the wet high protein product and the dry high protein product are combined at a ratio of about 25% to 45% dry high protein product.

7. The method of claim 1, wherein the wet high protein product has a water content of about 40% to 90% by weight.

8. The method of claim 1, wherein the high protein product is high protein thin stillage.

9. The method of claim 1, wherein the high protein product is high protein distillers wet grain with solubles (DWGS).

10. The method of claim 1, wherein the wet high protein product has a water content of about 60% to 80% by weight.

11. A method for drying high protein product from a fermentation process comprising:
    blending wet high protein product with dry high protein product to provide a blended high protein product;
    passing the blended high protein product through at least one venturi, then through an airflow generator and then a dryer, wherein the wet high protein product, the dry high protein product, and the blended high protein product include at least 40% protein by weight on a dry weight basis; and
    reducing moisture content of the blended high protein product during passing the blended high protein product through at least one venturi, then through an airflow generator, and a dryer; wherein the moisture content of the blended high protein product exiting the airflow generator is from about 35% to about 45% by weight.

12. The method of claim 11, wherein the blended high protein product has a water content of about 50% to 60% by weight.

13. The method of claim 12, wherein the wet high protein product has a water content of about 40% to 90% by weight.

* * * * *